United States Patent
Yoon et al.

(10) Patent No.: US 7,170,607 B2
(45) Date of Patent: Jan. 30, 2007

(54) GAS IDENTIFICATION DEVICE

(75) Inventors: Chang-No Yoon, Seoul (KR); Hyoung-No Yoon, Seoul (KR); Myung-Whan Chi, Seoul (KR); Min-Su Han, Seoul (KR)

(73) Assignee: Nanormics Incorporation Co., Ltd., Seoul (KR)

( * ) Notice: Subject to any disclaimer, the term of this patent is extended or adjusted under 35 U.S.C. 154(b) by 108 days.

(21) Appl. No.: 10/482,344

(22) PCT Filed: Jun. 28, 2002

(86) PCT No.: PCT/KR02/01240

§ 371 (c)(1), (2), (4) Date: Dec. 29, 2003

(87) PCT Pub. No.: WO03/002986

PCT Pub. Date: Jan. 9, 2003

(65) Prior Publication Data

US 2004/0179200 A1    Sep. 16, 2004

(30) Foreign Application Priority Data

Jun. 28, 2001    (KR) ................................ 2001-37759

(51) Int. Cl.
*G01N 21/61* (2006.01)
(52) U.S. Cl. ...................................... 356/437; 356/432
(58) Field of Classification Search ................ 356/432, 356/437
See application file for complete search history.

(56) References Cited

U.S. PATENT DOCUMENTS

| | | | |
|---|---|---|---|
| 3,819,276 A | * | 6/1974 | Kiess et al. ................ 356/414 |
| 4,058,725 A | | 11/1977 | Aine |
| 4,234,258 A | | 11/1980 | Margolis et al. |
| 4,557,603 A | | 12/1985 | Oehler et al. |
| 4,622,845 A | * | 11/1986 | Ryan et al. ................ 73/24.02 |
| 5,239,180 A | * | 8/1993 | Clarke .................... 250/339.11 |
| 5,348,002 A | * | 9/1994 | Caro .......................... 600/310 |
| 5,596,146 A | * | 1/1997 | Waller et al. ................. 73/590 |
| 5,753,797 A | | 5/1998 | Forster et al. |
| 5,933,245 A | * | 8/1999 | Wood et al. ................ 356/437 |
| 5,941,821 A | * | 8/1999 | Chou ......................... 600/316 |
| 5,956,143 A | * | 9/1999 | Kotidis ....................... 356/502 |
| 6,006,585 A | | 12/1999 | Forster |
| 6,148,658 A | | 11/2000 | Chou |

FOREIGN PATENT DOCUMENTS

| | | |
|---|---|---|
| EP | 0590 813 A1 | 9/1993 |
| EP | 0590813 A1 * | 9/1993 |

* cited by examiner

*Primary Examiner*—F. L. Evans
(74) *Attorney, Agent, or Firm*—Knobbe Martens Olson & Bear LLP

(57) ABSTRACT

An optical gas identification system including a measuring cell (20), a modulated light source (10), a microphone (22), and a signal amplifier (30). The light source (10) comprises a plurality of laser diodes (12) and can selectively illuminate the modulated light with specific wavelengths. The gas identification system can determine the object signal by use of the signal processor (70) and the database (60) with the various signal patterns.

11 Claims, 3 Drawing Sheets

GAS IDENTIFICATION DEVICE

This is the U.S. national phase under 35 U.S.C. §371 of International application PCT/KR02/01240, filed Jun. 28, 2002, which claims priority to Korean Patent Application No. 2001-0037759, filed Jun. 28, 2001.

BACKGROUND OF THE INVENTION (a) Field of the Invention

The present invention relates to photoacoustic spectroscopy, and more particularly, to applications that involve measurement of two or more gases or vapors in a mixture, and real-time gas monitoring.

(b) Description of the Related Art

Photoacoustic measurement is based on the tendency of molecules, when exposed to certain frequencies of radiant energy (e.g. infrared radiant energy), to absorb the energy and reach higher levels of molecular vibration and rotation, thereby reaching a higher temperature and pressure. When the radiant energy is amplitude modulated, the resulting dissipated heat fluctuations from energy absorption produce corresponding temperature and pressure fluctuations. A sensitive microphone can be used to generate an electrical output representing pressure fluctuations. The amplitudes of the acoustic signal and resulting electrical output are proportional to the intensity of the radiation and the concentration value of the absorbing gas.

A variety of these devices are known, for example U.S. Pat. No. 4,557,603 (Oehler et al), U.S. Pat. No. 4,818,882 (Nexo et al), U.S. Pat. No. 5,933,245 (Wood et al), U.S. Pat. No. 6,006,585 (Forster), and U.S. Pat. No. 6,148,658 (Chou et al). The devices have several components in common. In particular, laser or other energy sources produce radiant energy which is modulated either thermally (power on/off) or with a chopping device. The modulated energy is provided to a cell containing a gas or gas mixture that absorbs the radiant energy, leading to temperature fluctuations in the gas that track the modulation frequency. Temperature is not sensed directly, but rather pressure fluctuations that accompany the temperature fluctuations are detected by a sensitive microphone in the cell. The microphone output is detected at the modulation frequency to provide an electrical signal proportional to the gas concentration.

There is a need to determine the concentrations of one or more gases within a gas mixture. While this could be accomplished with two or more sensing systems, one devoted to each of the gases under study, a sharing of components among several systems would likely reduce costs. Accordingly there have been several proposals involving use of a single photoacoustic cell to detect two or more gases.

For example, the Nexo et al patent discloses a perforated disk with three sets of filter openings with different spacing between adjacent openings, for simultaneously filtering infrared light into different wavelengths "absorbed by $N_2O$, $SO_2$, and anesthetics, respectively" and modulating the wavelengths at three different frequencies. Signals corresponding to the various gases are said to be separated through electric filtration of the microphone signal.

The Oehler et al patent discloses a mechanical light modulator and monochromator having different interference filters said to enable simultaneous and separate detection of several components of a gas mixture. Oehler indicates that the interference with measurement by other gas components can be largely eliminated by using more than one narrow-band filter adapted to the maxima or flanks of the measuring gas or interfering components. Concentrations of different components are said to be determinable from the measurements performed with the different narrow band filters, with these filters being successively introduced into the path of the rays.

One disadvantage of these systems is the need to provide the radiant energy in extremely narrow bands. This requires either lasers for generating energy, or equipment designed to successively introduce different narrow-band filters into the light path between the source and photoacoustic cell. Either approach adds to the cost of the system. Further, it is difficult within the confines of these systems to distinguish between two gases with overlapping or coinciding absorption bands, or to determine the presence of an unknown absorbing gas.

Therefore, it is an object of this invention to provide the capability of separately measuring the concentration values of several gases having absorption lines or bands which may overlap or coincide with one another, or to detect the presence of another gas whose absorption bands or lines may overlap or coincide with those of the several gases of which sensing is desired.

The systems of the present invention do not suffer from the problems and drawbacks of other analysis techniques such as mass spectroscopy. Many current chemical analysis techniques are often unsatisfactory in that they are slow and expensive.

On-road vehicle emission inspections for pollutants are also important in order to intercept major pollution offenders and to improve overall air quality. Again, a fast, reliable, and accurate method of detection and a detector would be valuable tools to combat this source of air pollution.

Other examples of where a detector and method which is fast, economical, and reliable would be important are in sampling air proximate to a natural gas pipeline to determine the presence of leaks. Soil samples which may contain certain dense non-aqueous phase layer chemicals (DNALP) such as chlorobenzene and other pollutants are also in need of a detection method, system, and detector which is fast, economical, and reliable to detect the presence of such pollutants.

As another example, in the military or security fields, a fast; reliable, and accurate detector and method is needed to determine the presence of explosives or chemical warfare compounds. The foregoing are but several examples where there is a need for a reliable, inexpensive detector which does not suffer from the drawbacks of mass spectrometry or gas chromatography.

SUMMARY OF THE INVENTION

To achieve these and other objects, there is provided a gas identification device. The device includes a radiant energy source of various wavelengths, which measures photoacoustic signals when emitting light energy is absorbed, and then compares them with collected photoacoustic signal patterns.

Concretely, the device includes a measurement cell of stored gas samples, a light source assembly of a selected wavelength illuminating to a measurement cell, a microphone for detecting pressure fluctuations and transducing electric signals, a database of stored different signal patterns, a processor for comparing and analyzing signal patterns, and several diode lasers of different wavelengths emitting a fixed light source assembly that can move positions to illuminate a selected wavelength.

The measurement cell has a wall structure, preferably of aluminum or another metal, that encloses a generally cubic shape. The cell includes a space for storing a sample gas, and the cell body has opening front and rear windows and one or more valves for allowing sample gases in and out. The laser diodes in the light source assembly are moved by rotating or translating. Also, the cell includes a temperature sensor, and uses temperature corrections. The power of the laser diodes can be adjusted from 3 mW to 50 W, and the wavelengths of the emitting laser diodes are from 5 nm to 1650 nm.

DETAILED DESCRIPTION OF THE PREFERRED EMBODIMENTS

Figure 1:
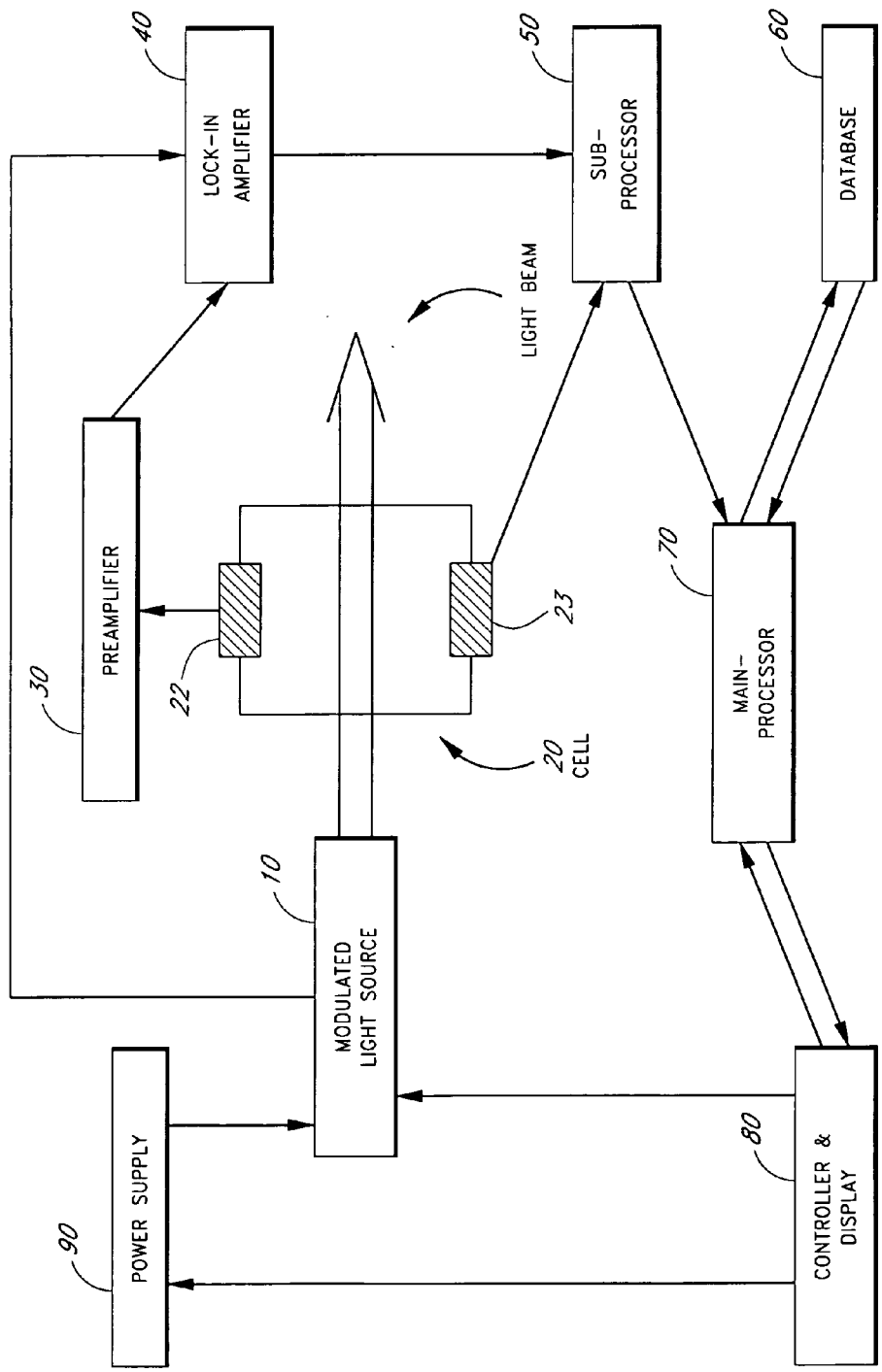
FIG. 1 shows a diagrammatic view of a gas identification device according to the present invention.

Referring to FIG. 1, the general aspects of the present invention will now be described. As shown, the present invention of a photoacoustic analyzer can comprise a light source (10) for providing a modulated light energy, a cell (20) for storing sample gases, a pre-amplifier (30) for amplifying a signal detected by a microphone (22), a lock-in amplifier (40) for detecting unique signals from the pre-amplifier (30), a temperature sensor (23) in the cell (20), a sub-processor (50) for processing temperature corrections from the temperature sensor (23), a database (60) for storing various mixture gas signal patterns, a main-processor (70) for comparing processed signals of the sub-processor (50) and analyzing signal patterns, a controller and display (80) for controlling the power supply (90) and light source (10) and displaying analysis results, and a power supply (90) for supplying power to the light source and other components.

The light source (10) is associated with various laser diodes emitting single wavelengths, each laser diode being a continuous wave (CW) type and emitting power from 3 mW to 50 W. The power of the laser diodes can be adjusted freely.

The cell (20) contains sample gases and includes penetrating windows for illuminating beam light sources (10), a microphone (22) for detecting pressure fluctuations, and a temperature sensor (23) for measuring the temperature inside the cell (20).

The pre-amplifier (30) amplifies electrical signals from the microphone (22) for further analysis.

The lock-in amplifier (40) filters out the noise of the amplified electrical signals and extracts only the photoacoustic signals.

The sub-processor (50) corrects lock-in amplifier (40) output signals using temperature sensor (23) output signals.

The main-processor (70) analyses and compares the signals with the stored database (60) with temperature-corrected photoacoustic signals. The database (60) stores many photoacoustic signal patterns of gases and can determine the concentration, kind, and ratio of a mixture of a gas. A statistical method is used for quantitative and qualitative analysis.

The controller and display (80) control the overall process and display processing order and results.

This gas identification device can be portable.

Figure 2:
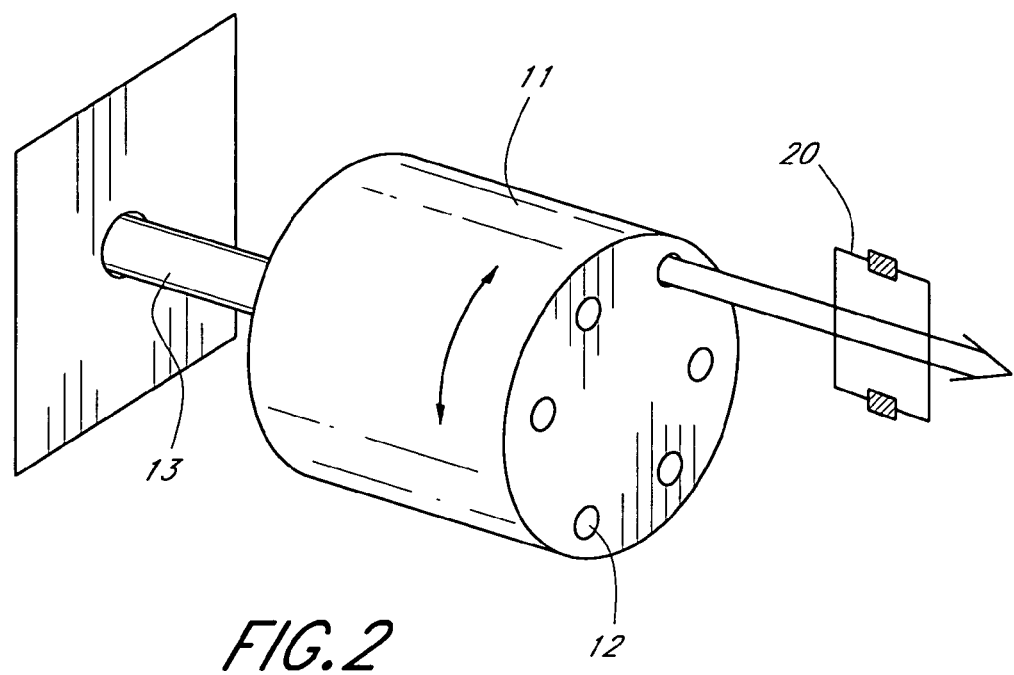
FIG. 2 and FIG. 3 show diagrammatic views of several light sources of a gas identification device.

Referring to FIG. 2, a cylindrical light source assembly (11) has several laser diodes emitting different wavelengths, and the light source assembly (11) is fixed by a propped axis (13). As the controller (80) can rotate light source assembly (11), a user can select various wavelengths for illuminating the cell (20). The light source assembly (11) can be rotated through rotating the propped axis (13). To vary the wavelength and laser power, the light source assembly (11) can have one more different light source assemblies (11) installed, or the light source assembly (11) can be changed.

Figure 3:
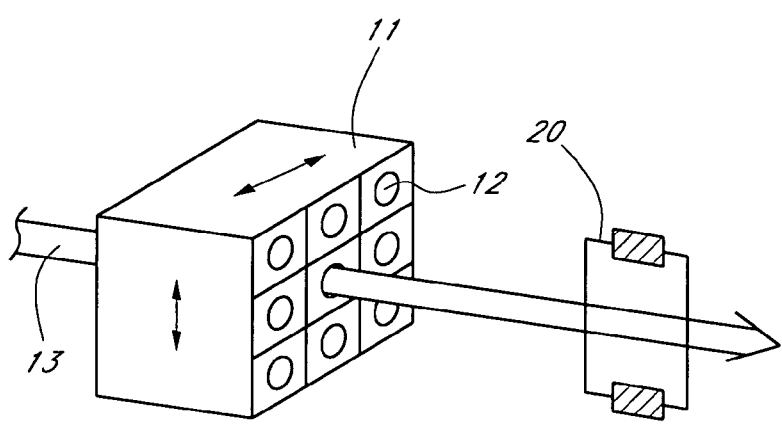

Referring to FIG. 3, a cubic light source assembly (11) has several laser diodes emitting different wavelengths installed, and the light source assembly (11) is fixed by the propped axis (13). As the controller (80) can move the light source assembly (11) right to left or up to down in parallel; the user can select various wavelengths for illuminating the cell (20). Additionally, to vary the wavelengths and laser power, the light source assembly (11) can have one more different light source assemblies (11) installed or different light source assemblies (11) can be exchanged with each other.

Each laser diode (12) emits a single wavelength, and its emitting power can be adjusted from 3 mW to 50 W. Accordingly, through selecting laser diodes, wavelengths and emitting power of the laser beam can be adjusted. The laser diodes (12) can emit a wavelength of 5 nm to 1650 nm, and the combination of laser diodes are different for different sample gases. As a result of the different combinations, relatively strong and efficient photoacoustic signals can be attained, and the intensity of the light beam can be changed by adjusting the light source power or by adjusting the distance from the light source assembly (11) to the cell (20).

Adjusting the power of the laser diode (12) and the modulating frequency is performed through electric circuits.

As previously stated, selecting wavelengths is performed through parallel or rotational movement of the light source assembly (11). Accordingly, the selected modulated laser beam can be directed into the cell (20) with any optical lens. While the light source assembly (11) is moving, all measuring processes are halted so that correct measurement can be performed.

Also, the light source assembly (20) can be fixed and the measurement cell (20) can be moved in the same manner. In this case, while the cell (20) is moving, all measuring processes are halted so that correct measurement can be performed.

With the above methods, without using any optical filter or monochromator, various wavelength and power light beam settings can be achieved using only the light source assembly (20).

Figure 4:
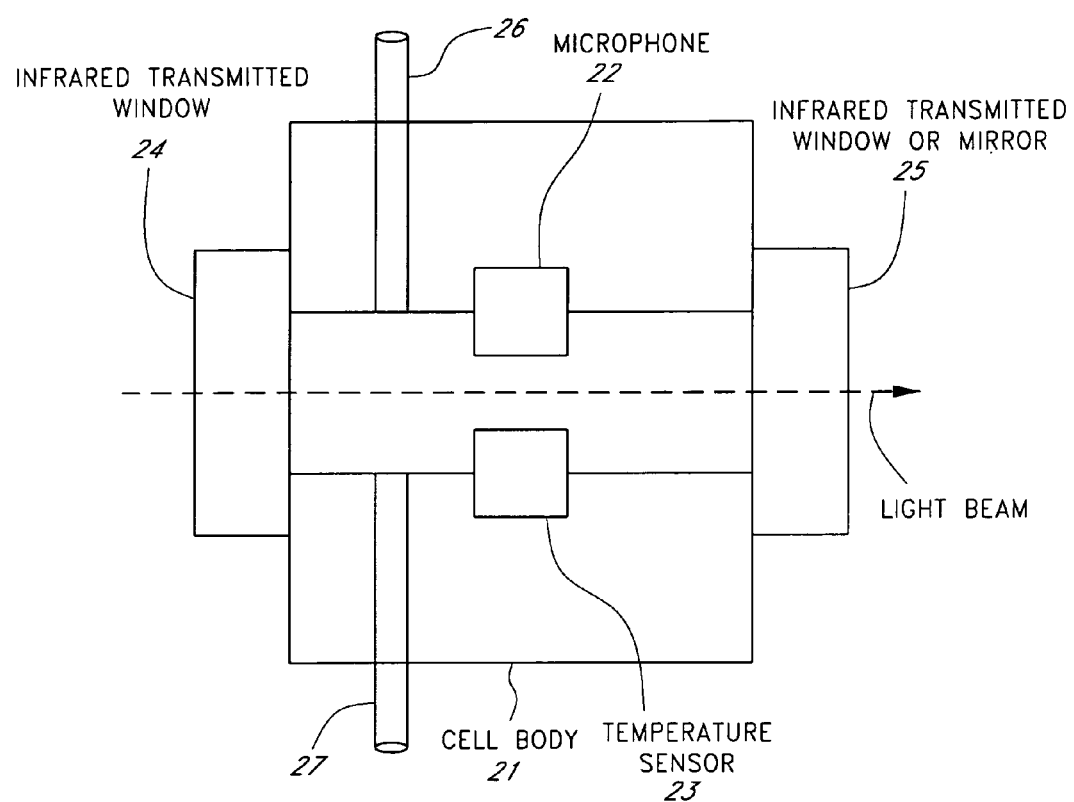
FIG. 4 shows a diagrammatic view of a measurement cell of a gas identification device.

FIG. 4 is a diagrammatic view of a measurement cell (20) of a gas identification device. The measurement cell comprises a cell body (21), a microphone (22), a temperature sensor (23), a front window (24), a rear window (25), and two valves (26, 27). The cell body (21) is a frame for the measurement cell (20), and it provides a space for the stored sample gases and a base for installing the compositional elements. The internal space of the cell (20) is cylindrical in shape, and the cell dimensions depend on the resonance frequency. In this invention, the resonance frequency ranges from 100 Hz to 1000 Hz. Also, the surface of the internal measurement cell (20) is mechanical polished to efficiently reflect the light beam. The microphone (22) is installed in the cell body to (21) detect pressure fluctuations and convert the pressure fluctuations into electrical signals. The temperature sensor (23) is installed in the cell body (21) to detect the temperature of the internal cell and send the measured information to the sub-processor (50). Two or more microphones can be installed in order to improve sensitivity. The front window (24) encloses the sample gas and is an infrared transmitted window. The rear window (25) encloses the sample gas and is also an infrared transmitted window or it is used to reflect a light beam made by a mirror in order to improve absorptional efficiency. Two valves (26,27) are installed to respectively admit or to exhaust the sample gases and to clean the internal cell (20).

What is claimed is:

1. An optical gas identification system, comprising:
   an optoacoustic cell containing a gas mixture;
   a light source for illuminating a modulated light with a specific wavelength to the gas mixture, the light source comprising an electric circuit for modulating frequency of lights and a plurality of laser diodes, each with a different wavelength;
   a microphone for detecting pressure fluctuations that occur from the gas mixture;
   a database for storing various signal patterns of the gas mixture;
   a signal processor for comparing an output signal with the signal patterns in the database; and
   a light assembly supporting the laser diodes,
   wherein the light assembly in which the laser diodes are located is moved by rotating.

2. The optical gas identification system of claim 1, wherein the cell contains two windows for allowing passage of transmitted light, and gas valves for respectively injecting and exhausting the gas mixture.

3. An optical gas identification system comprising:
   an optoacoustic cell containing a gas mixture;
   a light source for illuminating a modulated light with a specific wavelength to the gas mixture, the light source comprising an electric circuit for modulating frequency of lights and a plurality of laser diodes, each with a different wavelength;
   a microphone for detecting pressure fluctuations that occur from the gas mixture;
   a database for storing various signal patterns of the gas mixture;
   a signal processor for comparing an output signal with the signal patterns in the database; and
   a light assembly supporting the laser diodes,
   wherein the light assembly in which the laser diodes are located is moved in a parallel fashion.

4. The optical gas identification system of claim 1, wherein the laser diodes (2–100) in the light assembly have different wavelengths and powers.

5. The optical gas identification system of claim 1, wherein the optoacoustic cell comprises a thermal sensor and the signal processor which calibrates the output signal from the cell with the thermal signal of the thermal sensor.

6. The optical gas identification system of claim 1, wherein the laser diodes from which the light emanates are changed from 3 mW to 50 W.

7. The optical gas identification system of claim 1, wherein the laser light has specific wavelengths from 5 nm to 1650 nm.

8. The optical gas identification system of claim 3, wherein the laser diodes (2–100) in the light assembly have different wavelengths and powers.

9. The optical gas identification system of claim 2, wherein the optoacoustic cell comprises a thermal sensor and the signal processor which calibrates the output signal from the cell with the thermal signal of the thermal sensor.

10. The optical gas identification system of claim 2, wherein the laser diodes from which the light emanates are changed from 3 mW to 50 W.

11. The optical gas identification system of claim 2, wherein the laser light has specific wavelengths from 5 nm to 1650 nm.

* * * * *